(12) United States Patent
Bacanovic et al.

(10) Patent No.: US 8,641,581 B2
(45) Date of Patent: Feb. 4, 2014

(54) ERGOMETRIC TRAINING DEVICE

(75) Inventors: Milan Bacanovic, Vienna (AT); Dusan Adamovic, Vienna (AT)

(73) Assignee: Wattbike IP Limited, Nottingham, Nottinghamshire (GB)

( * ) Notice: Subject to any disclaimer, the term of this patent is extended or adjusted under 35 U.S.C. 154(b) by 313 days.

(21) Appl. No.: 12/675,150

(22) PCT Filed: Aug. 28, 2008

(86) PCT No.: PCT/AT2008/000306
§ 371 (c)(1),
(2), (4) Date: Feb. 25, 2010

(87) PCT Pub. No.: WO2009/026604
PCT Pub. Date: Mar. 5, 2009

(65) Prior Publication Data
US 2011/0111923 A1    May 12, 2011

(30) Foreign Application Priority Data

Aug. 30, 2007  (AT) ................................ A 1363/2007
Aug. 30, 2007  (AT) ................................ A 1364/2007

(51) Int. Cl.
*A63B 22/06* (2006.01)
*A63B 69/16* (2006.01)
*A63B 71/00* (2006.01)

(52) U.S. Cl.
USPC .................................. 482/57; 482/8; 482/900

(58) Field of Classification Search
USPC ........... 482/1–9, 51, 57–65, 72–73, 111–113, 482/900–903; 601/23, 36
See application file for complete search history.

(56) References Cited

U.S. PATENT DOCUMENTS 4,141,245 A * 2/1979 Brandstetter ............... 73/862.46
4,168,758 A * 9/1979 Holt .............................. 180/206
(Continued)

FOREIGN PATENT DOCUMENTS

DE       4227586      2/1994
EP       0323056      7/1989
(Continued)

OTHER PUBLICATIONS

International Search Report, mailed Apr. 15, 2010, completed by EP ISA.

(Continued)

*Primary Examiner* — Oren Ginsberg
(74) *Attorney, Agent, or Firm* — Renner, Otto, Boisselle & Sklar, LLP

(57) ABSTRACT

A stationary, ergometric exercise apparatus including a hand/foot-operated drive with two drive elements that are operated alternately and a measuring device for measuring the drive force applied to the drive force includes a measuring device for measuring the angular position of the drive, having a pair of sensor devices which are arranged in positions opposite to each other relative to a wheel that is joined to the drive so as to be synchronous in motion with it, which positions each correspond to a position in motion of a load alternation between the two drive elements. A computer receives the signals from the force measuring device and calculates the temporal progress of the drive force, as well as variables that can be derived from it, and alternately output a dedicated right or left limb reading for a person in training depending on the load alternation notified by the measuring device.

18 Claims, 4 Drawing Sheets

(56) References Cited

U.S. PATENT DOCUMENTS

| | | | |
|---|---|---|---|
| 4,589,656 A | | 5/1986 | Baldwin |
| 4,934,692 A | | 6/1990 | Owens |
| 5,027,303 A | | 6/1991 | Witte |
| 5,051,638 A | | 9/1991 | Pyles |
| 5,165,278 A | * | 11/1992 | Huszczuk et al. ......... 73/379.06 |
| 6,199,021 B1 | * | 3/2001 | Cote et al. ....................... 702/44 |
| 6,302,827 B1 | | 10/2001 | Stevens |
| 6,356,848 B1 | * | 3/2002 | Cote et al. ....................... 702/44 |
| 6,857,975 B2 | * | 2/2005 | Kitamura ......................... 474/70 |
| 7,806,006 B2 | * | 10/2010 | Phillips et al. ............ 73/862.338 |
| 7,833,135 B2 | * | 11/2010 | Radow et al. ................... 482/57 |
| 7,862,476 B2 | * | 1/2011 | Blau et al. ......................... 482/8 |
| 2003/0171190 A1 | * | 9/2003 | Rice ................................ 482/57 |
| 2006/0003872 A1 | * | 1/2006 | Chiles et al. ................... 482/57 |

FOREIGN PATENT DOCUMENTS

| | | |
|---|---|---|
| GB | 2409651 | 6/2005 |
| JP | 60-171052 | 9/1985 |
| JP | 62-46193 | 10/1987 |
| JP | 2004-173862 | 6/2004 |
| RU | 2081645 C1 | 6/1997 |
| WO | 2007/015096 | 2/2007 |
| WO | 2009/026604 | 3/2009 |

OTHER PUBLICATIONS

Japanese Examination Report dated Nov. 6, 2012.
Japanese Office Action.
English version of the pertinent portion of Japanese Office Action.

* cited by examiner $F_p$ [N]

ERGOMETRIC TRAINING DEVICE

CROSS REFERENCE TO RELATED APPLICATIONS

The present application is a U.S. National Stage Application of PCT Application Serial No. PCT/AT 2008/000306, filed on Aug. 28, 2008, which claims priority from Austrian Patent Application Serial No. A 1363/2007, filed on Aug. 30, 2007 and Austrian Patent Application Serial No. A 1364/2007, filed on Aug. 30, 2007, all of which are incorporated by reference in their entireties.

BACKGROUND OF THE INVENTION

The invention concerns an ergometric, stationary piece of exercise apparatus with a manually-operated (by hand or foot) drive with two drive elements that are operated alternately, wherein the drive is joined to a flywheel by a gear mechanism, as well as to a measuring unit for measuring the drive force applied to the drive, or the torsional force (torque) related to the drive force, and a measuring device for measuring the position in motion, in particular angular position, of the drive. The drive elements are preferably pedals, similar to those on a bicycle, but can however also be of a different kind, such as e.g. the stepping platforms of a so-called stairmaster.

A piece of training equipment of this kind is described in U.S. Pat. No. 5,027,303. The moment is measured by means of resistance strain gauges that are attached to loaded components of the pedal configuration in order to measure parameters such as moment, work, power, angular velocity and time per revolution. In this way measurement of the whole moment, as well as of the moments on the left and right pedals (left and right legs respectively) is carried out; from this, work performed and power can be calculated.

EP 0 925 096 B1 describes an electronic exercise system with a monitor for physical activity that has a sensor and display device, which records and displays physical data during a first period. The exercise apparatus has a resistance generator, e.g. an eddy-current brake, and a control that uses the data displayed about physical activity to control the operation of the exercise apparatus.

U.S. Pat. No. 5,354,251 describes an exercise machine in which a seat and a spring-loaded rotating shaft are attached in an elongated frame. The rotating shaft is joined to a flywheel and has resistance devices. Disclosed as resistance devices are e.g. a centrifugal brake, a wind wheel-like, open-worked flywheel, as well as and eddy-current brake wheel, into which a wind wheel is integrated.

Further exercise devices are described in US 2002/0004439 A1, US 2007/0117680 A1, U.S. Pat. Nos. 5,611,759 and 5,749,807.

A measurement of moment on the chain of a bicycle emerges from JP 05 201374 A. A tension detector is arranged on the upper chain section to measure the elasticity, namely a gear wheel that touches the chain on the outside and a resistance strain gauge that measures the force exercised on the gear wheel by the chain.

DE 199 19 154 A1 describes a method and a device for applying a preload force to an endless drive element, in particular a chain. A gripper is pressed by means of a chain tensioning device onto the chain from the outside with a predetermined force. The preload force on the chain so arising is set via control electronics depending on sensor data concerning oscillation data or other standard parameters.

U.S. Pat. No. 4,141,245 describes a device for measuring mechanical work and power, which is transferred onto a drive element between two drive wheels. A force measuring element with a roller is pressed by means of spring force against the drive element, and the degree of displacement serves to measure the tensile force transferred. Various embodiments contain a roller touching on the on the inside or the outside, or a combination of at least one roller in the inside and one on the outside.

Further measuring equipments for measuring the drive moment in a drive system, e.g. a bicycle, are presented in U.S. Pat. No. 4,909,086 and US 2007/0099735 A1.

DE 42 27 586 A1 shows a pedal exercise device with separate force measurement for the two pedal arms, namely by means of a resistance strain gauge on each pedal arm, and with an angle transmitter, through which an evaluation of the path of motion is made possible, e.g. as a polar diagram. DE 44 35 174 A1 additionally suggests arranging the resistance strain gauge diagonally on the pedal arm in question.

Further proposals for force measurement in the operation of pedal motion are described in US 2007/0149364 A1, U.S. Pat. No. 5,573,481, WO 02/47551 A2 and EP 1 362 552 A1.

These known exercise and measuring apparatuses aim to measure the force or torque expended by the person training by various methods, which are nevertheless often time-consuming and complex. The known methods are particularly time-consuming if a differentiated view of various sections of the process, namely a breakdown between the two feet (or the two hands on hand-operated devices), is desired.

BRIEF SUMMARY OF THE INVENTION

The present invention creates exercise apparatuses in which a measurement of the applied force or torsional force is apportioned to the movements happening on the left/right.

This is achieved based on an exercise apparatus of the type named initially, wherein the measuring device for measuring the position in motion according to the invention has a pair of sensor devices that are arranged in positions located opposite to each other relative to a wheel that has been joined to the drive so that it moves synchronously to it, positions that each correspond to a position in motion of a load alternation between the two drive elements.

This solution permits in a simple way a detection of the load alternation between the left and the right limbs, and so a distinction between the forces applied by them, or work generated by them, as the case may be. Moreover, it allows a simplification of the measuring procedure as well as a reliable evaluation of the data recorded on force as a function of the foot position, or rather the angle of rotation. The wheel is, e.g., a gear wheel attached to the pedal shaft in a rotationally fixed manner, or it can be joined to the pedal shaft via a gear mechanism, so long as the conversion makes it possible to have an adequate conclusion about the angularity of the wheel onto the position in motion of the drive.

In an exemplary embodiment of the invention, which depicts a particularly effective implementation of the approach underlying the invention, the two sensor devices are designed as sensor pieces attached on the wheel in positions lying opposite each other; moreover, at least one sensor device is arranged in a fixed position, which makes detectable the passing of the sensor piece through a specific angular position or the wheel, wherein the angular position corresponds to a position in motion of a load alternation between the two drive elements.

It is, however, also suitable if the two sensor devices are designed as sensors and at least one additional sensor piece attached to the wheel is provided, wherein by means of the sensors the passing of the at least one sensor piece by specific angular positions, located opposite each other, of the wheel is detectable, wherein each angular position corresponds to a position in motion of a load alternation between the two drive elements.

For an effective, contact-free detection of the moveable parts it is advantageous if the sensor pieces are magnets, in particular permanent magnets, and the sensors are magnet field sensors.

In order to additionally achieve a simplification of the measuring device used for measuring the force applied, it is advantageous if the measuring unit for measuring the drive force is an arm attached to a traction mechanism, in particular to a chain, of the gear mechanism, which slightly presses on the side of the traction mechanism and has a measuring sensor for measuring the pulling force thereby exerted by the traction mechanism.

An evaluation system can advantageously be provided in order to receive signals from the measuring unit concerning the drive force or related torsional force applied, and to calculate the temporal progress of the drive force or torsional force, as well as variables derivable from that quantity, on the basis of the signals delivered by the measuring unit, and to show them continuously. The evaluation device can furthermore receive signals from the measuring device concerning times of load alternation and allocate the calculated variables alternately to a person in training's right or left limb depending on the load alternation reported by the measuring equipment. The output of the variables calculated in this way can therefore be carried out apportioned to the right or left limb on the basis of the signal of the measuring device concerning times of load alternation. An uncomplicated determination and automated output of the training power apportioned to left/right succeeds through this further development.

It is furthermore desirable that the speed-dependent resistance that the person in training must overcome on the exercise device according to the invention be as true to nature as possible, i.e. correspond to the resistance on a roadworthy bicycle. To this end, it is advantageous if the flywheel has a device that is slowed down by air resistance and is joined to an electro-magnetically-acting brake. The device slowed down by air resistance can be a paddle wheel joined to the flywheel in rotationally locked manner. Moreover, the paddle wheel can have many blades aligned parallel to the axis of rotation.

In order to be able to additionally set the air resistance effect according to need, it is advantageous if the device slowed down by air resistance is located in a housing that has a means for setting the quantity of airstream moved by the motion of the flywheel. For example, the housing can have openings, the size and air permeability of which can be set and by means of which the airstream going though the housing can be set.

BRIEF DESCRIPTION OF THE DRAWINGS

In what follows, the invention will be described in more detail on the basis of a non-limiting exemplary embodiment, which is shown in the attached drawings. The drawings show.

DETAILED DESCRIPTION OF THE PRESENT INVENTION

Figure 1:
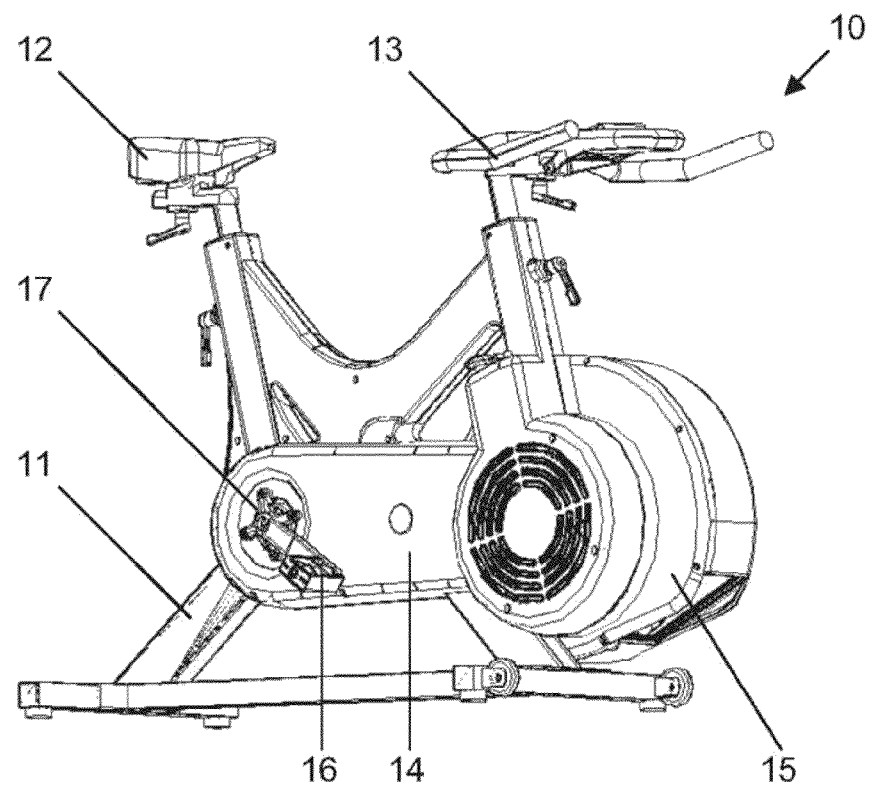
FIG. 1 a perspective view (from right front) of the training device according to the exemplary embodiment of the invention.
Figures 2, 3:
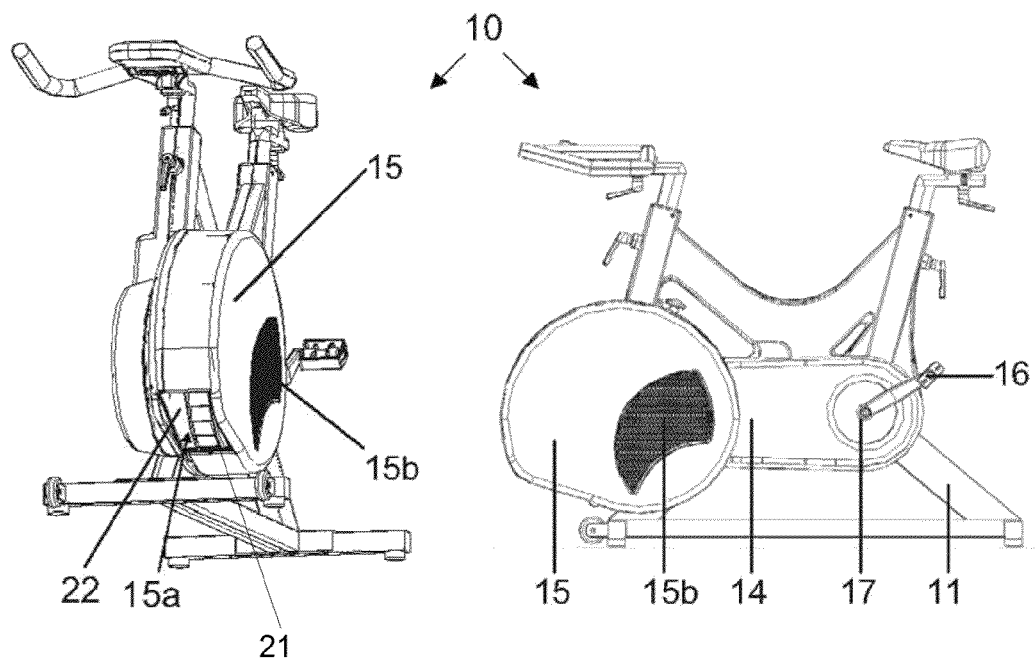
FIGS. 2 and 3 the training device in a further oblique view and a side view of the left side.

The exemplary embodiment discussed in what follows concerns a stationary ergometric bicycle training device, which is shown in FIGS. 1 to 3 in various views. The training device 10 can be used e.g. as a home exercise machine, as a training device in a fitness studio or for use in elite sport, or also in the medical field.

The training device 10 has a bicycle-like rack frame 11 with a seat 12 and handlebars 13, the positions of each of which can be set, while a training cycle is nevertheless fixed. In the foot area is located a housing 14, which in its front area has a wheel guard 15, as well as a pair of pedals 16. The pedals 16 are attached to a pedal shaft 17 in the known way and are connected via a gear mechanism with resistance mechanisms, which are accommodated into the wheel guard 15 as described below.

Figure 4:
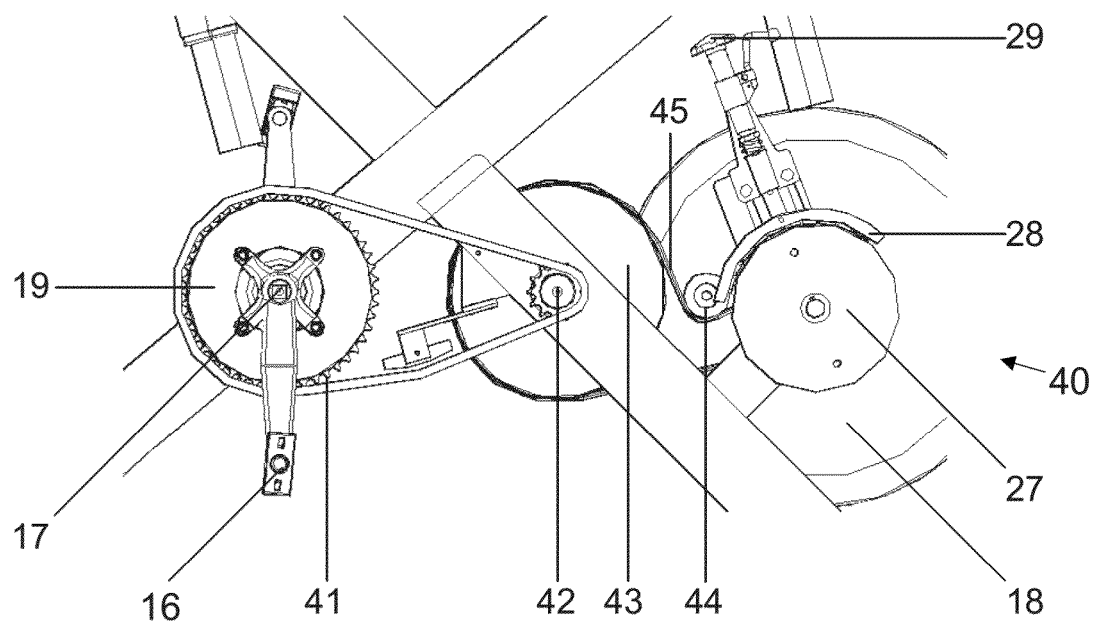
FIG. 4 the gear mechanism of the training device in a detailed view (side view of the right without housing)

With reference to FIG. 4, the gear mechanism 40 is, in the shown exemplary embodiment, a combination of two traction drives, namely a gear drive with a belt drive, through which a high translation of the motion of the pedal 16 to the flywheel 18 is achieved. The pedals 16 are joined inelastically via the pedal shaft 17 to a gear wheel 19, that drives a pinion wheel 42 via a chain 41. The pinion wheel 42 is in turn joined to a disc wheel 43, which drives the flywheel 18 via a belt 45 stretched by means of an ancillary wheel 44.

The embodiment shown has available a measuring system with a measuring precision of 2% or better. It serves to measure the force used up by the user and the pedal speed and is joined with a computer system to show and evaluate the data measured.

Measurement of Force

Figure 5:
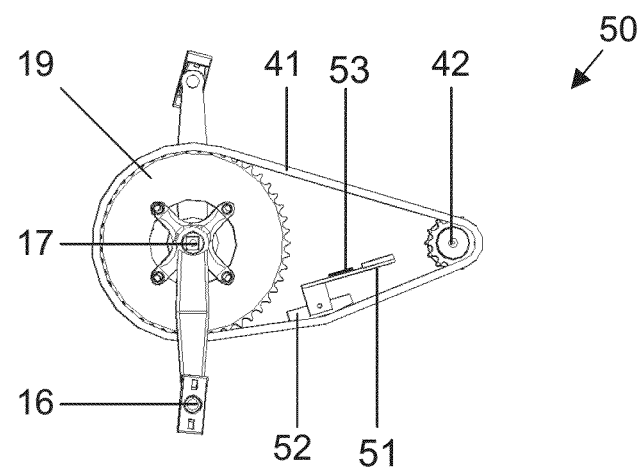
FIG. 5 a detail of FIG. 4 showing the force measurement on the gear mechanism chain.

As shown in FIG. 5, a measuring unit 50 is advantageously provided in the first traction drive, for measuring the force that the person in training applies via the pedal drive onto the chain 41. The pedal length being fixed and known, the drive force can be calculated directly into the acting torque (moment of force, 'torsional force'), and in this respect is equivalent.

The measuring unit is advantageously implemented as a beam in bending with a measuring stretch strip, which slightly deflects the chain and measures the restoring force. An arm 51 attached to the frame 11 bears on its end a glide 52 that is e.g. constructed out of plastic. The glide is applied onto the chain 41 e.g. on the inside, similar to a chain stretcher, and pushes the chain slightly outwards. If the chain is under tension as a result of force applied by the person in training, then a tangential component of the force results onto the plastic glide and onto the glide acts a restoring force that is proportional to the chain tension and hence the torsional force. The elastic bending of the arm 51 thereby resulting is measured by a measuring sensor, e.g. a stretch measuring strip 53. The signal of the measuring sensor is electronically evaluated, as is further described below.

In order to calibrate the force measurement, a weight of known size is attached to one of the pedals 16, and turning is mechanically blocked on the flywheel 18 or the flywheel disc 27 (FIG. 7) by means of a blocking agent (not shown), for example. The force measured in this circumstance serves as a basis for the calibration of the force measuring system by comparison with the known force applied by the weight.

Resistance Mechanism

Figure 6:
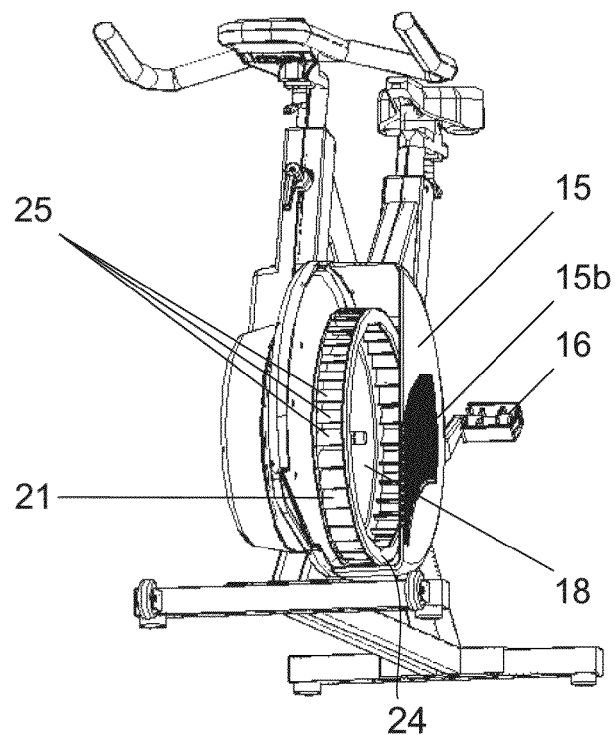
FIG. 6 a cross-section of the wheel drum of the training device.

Referring to FIG. 6, the flywheel 18 driven by pedal motion via the gear mechanism 60 has an air paddle wheel 21 that is set so that it cannot be rotated about the circumference of the flywheel blade. The air paddle wheel 21 is located in its own container as a part of the wheel guard 15.

Figure 7:
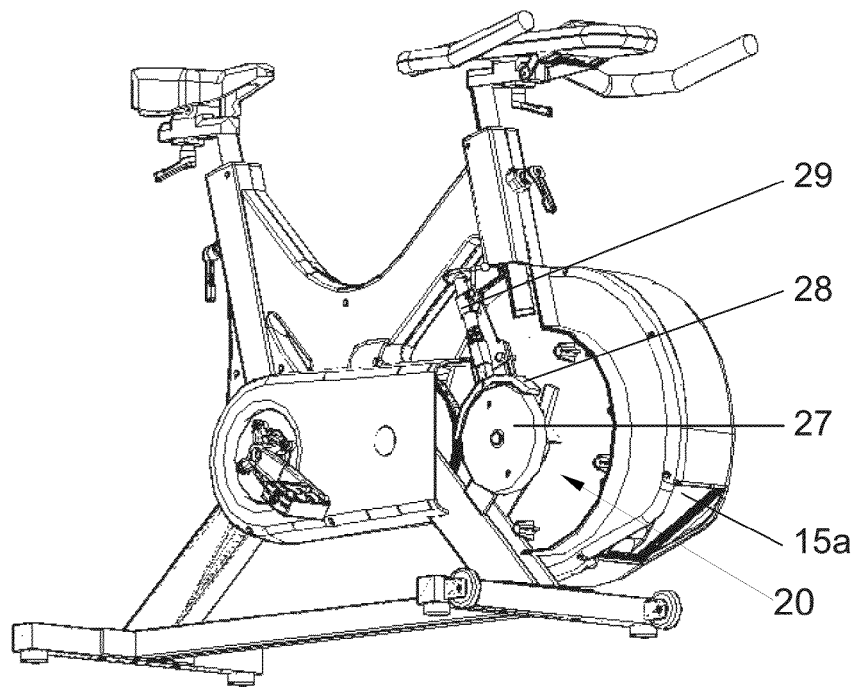
FIG. 7 a view of the training device with opened magnetic brake.

As is visible in FIG. 7, in the shown exemplary embodiment an eddy current brake 20 is arranged on the same axle as the flywheel 18, preferably opposite to it. The eddy current brake 20 is e.g. a magnetic brake, in which a metallic flywheel disc 27 cooperates with placeable (permanent) magnets 28 in the known way; alternatively, other electromagnetically-acting brakes can also be implemented. In the shown exemplary embodiment, the magnets are arranged on a steel bracket along a circumferential piece of the disc 27 and are positioned towards the disc 27 or away from it with the help of a placing mechanism 29. The disc 27 consists of steel, for example, which is sheathed with a copper ring. In order to be able to completely block the rotation, two holes 27 are provided in the disc, for example, holes into which a (not shown) blocking pin held in the housing or on the frame can be introduced from the side.

The resistance mechanisms of the training equipment according to the invention replicated those that arise during a cycling journey. The resistances acting while cycling are (a) air resistance, (b) friction of the mechanical parts inside the bicycle and (c) rolling resistance between tires and the surface of the road or incline of the area. As a rule, air resistance makes up an overwhelming proportion—often more than 90%—of the total resistance and grows quadratically with speed. Therefore, the power generated grows cubically with speed. The friction in the bicycle and the rolling resistance grow linearly with speed, which corresponds to power with a quadratic speed dependency.

In the training device 10, a combined braking system is used to simulate these two types of resistance. It has two brake subsystems, namely as described already a braking mechanism acting via air braking in the form of the wheel 21 and an electromagnetically-acting brake 20. In this way, a realistic modeling of the resistance ratio of a bicycle succeeds, giving the feeling of moving on a 'normal' bicycle. The two subsystems can be set up independently of each other. They have no influence on the measuring equipment described further below. The combination of the two brake subsystems makes possible a large range of resistance, which results depending on the frequency of pedaling. No external energy sources are required.

Once again referring to FIG. 6, the air paddle wheel 21 has an essentially cylinder ring-like shape. Along the circumference, a number of paddle blades 25 are arranged at regular distances between two retainer rings 24 on the side, which paddle blades are each arranged as blades aligned parallel to the axis of rotation of the wheel 21 and at an angle other than 90° to the radius. When the wheel 21 turns, then the blades 25 move the surrounding air inwards. In this way, air is sucked through the side window 15b and forced out again via the opening 15a (FIG. 2) found on the lower front side of the wheel guard 15; hence the wheel 21 is slowed down by the resulting air circulation.

In contrast to known training devices with an air brake, the resistance in the equipment shown can be set by regulation of the air intake on the stator side (FIG. 3), namely by more or less extensive closing of the opening 15a by means of a flap 22 and/or setting of the side window 15b with regards to its air permeability, for example in the manner of a Venetian blind. In this way the braking effect deriving from air resistance can be set within a large range. In particular, by closing the opening 15a and the window 15b, the resistance can be set to a minimum value near to zero, so that the mechanical friction essentially simply remains in the system.

The resistance for each of the two braking subsystems can be set by these measures. In the exemplary embodiment shown, a resistance effect of 0 to 5000 W can be chosen.

Measuring the Pedal Speed

Figure 8:
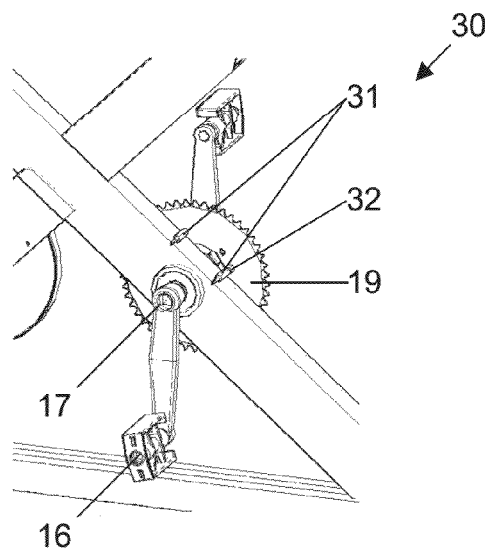
FIGS. 8 and 9 detailed views of the left on the area of the pedal arrangement, with partially removed housing, so that the sensors for measuring the pedal position are visible, wherein in FIG. 7 the supporting bar and the axle box are left out.
Figure 9:
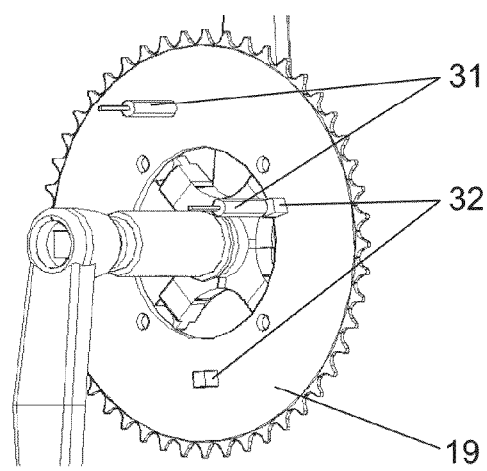

In FIGS. 8 and 9, the sensor equipment 30 for measuring the pedal speed is depicted. Two magnetic field sensors 31, e.g. reed switches, are arranged fixed next to the pedal gear wheel 19. Two permanent magnets 32 are arranged in precisely opposite positions on the gear wheel 19, so that in the course of a rotation of the gear wheel 19 each magnet 32 passes each of the sensors 31 once, and so generates e.g. a signal impulse. The signal so arising is delivered to evaluation and permits precise measurement of the number of revolutions per minute, as well as—via the crank length—the pedal speed.

Both sensors 31 and the magnets 32 belonging to them correspond to each other in pairs and are each positioned in different radial distances from the axle (in order to exclude the possibility of activation of one sensor on each side by the magnet of the other sensor). The magnets are arranged with regard to their angular position to the sensors belonging to each of them relative to the positioning of the pedals 16 in such a way that a signal impulse from a sensor 31 is then given in each case if the force alternation is carried out from the left to the right pedal, or the other way around. As can be recognised from FIGS. 8 and 9, in the shown positioning of 0° (right pedal perpendicular upwards) one magnet is exactly in position with the sensor allocated to it, while the other magnet is located exactly opposite the sensor allocated to it. This enables an apportioning of the measurement and separate allocation to the left and right feet, and a right/left evaluation of the force and power applied by each foot, as well as a comparison of the two foot powers (balance).

By the allocation of the sensor-magnet pair, so that they are aligned for detection of the positions of the load alternation, the beginning of the measuring cycle, which conventionally consists of a succession of discrete measuring points, can be established. A pedal sequence on the sensor positions—hence in a load alternation—is chosen as the beginning of a series of measurements, so that on the one hand a measuring point can also happen upon load alternation (where in particular with inexperienced cyclists a minimum of the force applied is to be expected), and on the other hand the series of measurements is measured between successive sensor cycles is measured at essentially constant speed; since after a load alternation the angular velocity of the pedal motion is empirically essentially constant, in contrast to which the speed between the individual stepping cycles can often change. This enables to simplify the measuring process as well as to improve reliability of evaluation of the data recorded regarding the force as a function of foot position, in particular the angle of rotation.

Evaluation

Figure 10:
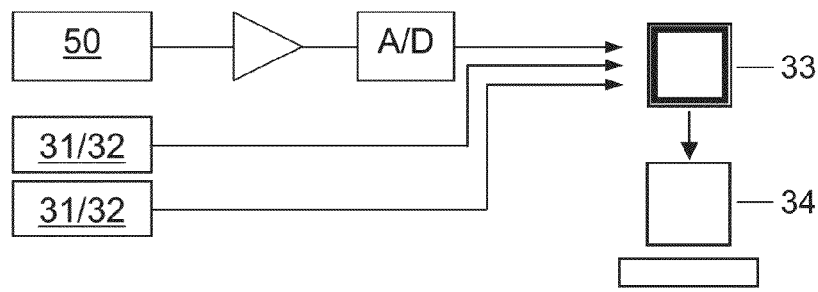
FIG. 10 a block diagram of the signal and data evaluation.
Figure 11:
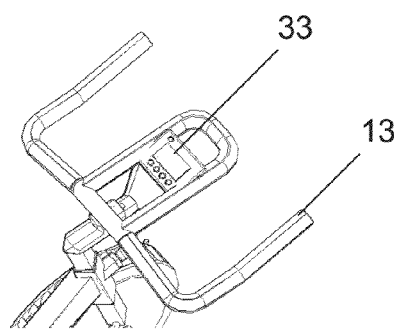
FIG. 11 a view of the handlebars of the training device with a display.

As is shown in FIG. 10, the sensor signals delivered by the force measuring sensor (stretch measuring strip) 53 and by the sensors 31 allocated to pedal measuring are amplified, digitized by means of analogue-digital converters and conveyed to an electronic evaluation, e.g. a training display 33 found on the handlebars (FIG. 11) and/or an allocated computer system 34. In the computer system 34, the signals are converted in a time-dependent process into the drive force applied to the pedals, for example with a data rate of 100 data points per second. Moreover, the signals can be displayed in real time and/or saved. The data can then be recalled and edited at a later time. The display of the data is advantageously carried out in a way related to pedal rotation and/or in a polar display such as is shown in FIG. 12.

Figure 12:
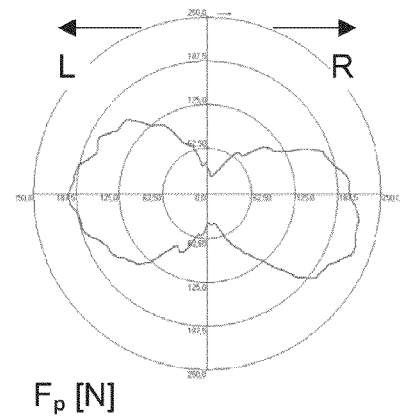
FIG. 12 an example of a depiction of the drive force depending on the angle of rotation (polar form).

FIG. 12 shows an example of a measured pedal force $F_P$ (in N; the outer circle corresponds to 250 N) over a whole rotation with the pedal, as a function of the angle of rotation in a polar diagram. The angles shown correspond directly to the angle of the pedal that is moved in a clockwise direction, wherein 0° corresponds to a positioning of the right pedal perpendicularly upwards. It is also worth mentioning that, in particular with trained sportsmen and women, a synergy between the two feet arises, and the better the coordinated ability is calibrated for people in training, the rounder is the figure of the curve $F_P$.

In the computer system 40, by means of suitable ergometric software the analysis of the data measured and the graphic display is implemented on the screen, for example:

Calculation and display of the pedal moment,
Force as a function of foot position,
Number of revolutions per minutes,
Speed (calculated on a notional bicycle speed),
Power (W),
Average power,
Energy (kJ, by integration),
Balance between left and right foot (in %),
Heart rate (via additional sensor belt worn by the user),
Statistical analyses.

Of course, the invention is not limited to the exemplary embodiment described, but rather extends to all embodiments falling within the range of the claims. In particular, the exercise equipment according to the invention can also have drive elements other than pedals, for example stepping platforms such as on a stairmaster or a pair of hand grips that are to be operated alternately. Here, the motion is converted in a known way mechanically via a gear mechanism into the rotational motion of a drive wheel.

The invention claimed is:

1. A stationary ergometric exercise apparatus with a hand- or foot-operated drive with two alternately-operable drive elements wherein the drive is joined to a flywheel by means of a gear mechanism; and the apparatus includes a measuring unit for measuring at least one of a drive force applied via the drive and a torque related to the drive force, and a measuring device for measuring an angular position of the drive, wherein the apparatus includes a wheel joined to the drive so as to be synchronous in motion with the drive and the measuring device includes a pair of sensor devices arranged in positions relative to the wheel whereby a signal is generated when the wheel is located at each of two specific angular positions, the positions being located 180° apart and corresponding to positions in motion of a load alternation between the alternately-operable drive elements, and further characterized by an evaluation device configured to receive signals from the measuring unit concerning the drive force applied and/or torque related to it, and to calculate and continuously output temporal progress of the drive force and/or related torque, as well as variables derivable from the drive force, on the basis of the signals delivered by the measuring unit, and wherein the evaluation device is configured to receive signals from the measuring device identifying times of load alternation between the alternately operable drive elements, and use the times of load alternation identified by the measuring device to apportion the variables calculated on the basis of the signals delivered by the measuring unit alternately to a right or left limb of a person in training.

2. The stationary ergometric exercise apparatus according to claim 1, wherein the measuring device includes a pair of sensor pieces attached to the wheel and at least one sensor positioned in a stationary location relative to the wheel, the sensor pieces being movable with the wheel relative to the at least one sensor on operation of the drive by means of which each of the sensor pieces is detected passing a sensor when the wheel is located at a respective one of two specific angular positions, the positions being located 180° apart and corresponding to the positions in motion of a load alternation between the alternately-operable drive elements.

3. The stationary ergometric exercise apparatus according to claim 2, wherein the sensor pieces are magnets and the sensors are magnetic field sensors.

4. The stationary ergometric exercise apparatus according to claim 2, wherein the measuring unit for measuring the drive force is an arm applied to a traction mechanism, in particular to a chain, of the gear mechanism, the arm pressing slightly on the side of the traction mechanism, and the measuring unit further including a measuring sensor to measure at restoring force applied by the traction mechanism to the arm.

5. The stationary ergometric exercise apparatus according to claim 1, wherein the measuring device includes a pair of sensors positioned in stationary locations relative to the wheel and at least one sensor piece attached to the wheel, the at least one sensor piece being movable with the wheel relative to the sensors on operation of the drive by means of which the sensors detect a passing sensor piece when the wheel is located at a respective one of two specific angular positions, the positions being located 180° apart and corresponding to the positions in motion of a load alternation between the alternately-operable drive elements.

6. The stationary ergometric exercise apparatus according to claim 5, wherein the sensor pieces are magnets and the sensors are magnetic field sensors.

7. The stationary ergometric exercise apparatus according to claim 5, wherein the measuring unit for measuring the drive force is an arm applied to a traction mechanism, in particular to a chain, of the gear mechanism, the arm pressing slightly on the side of the traction mechanism, and the measuring unit further including has a measuring sensor to measure a restoring force applied by the traction mechanism to the arm.

8. The stationary ergometric exercise apparatus according to claim 1, wherein the measuring unit for measuring the drive force is an arm applied to a traction mechanism, in particular to a chain, of the gear mechanism, the arm pressing slightly on the side of the traction mechanism, and the measuring unit further including a measuring sensor to measure a restoring force applied by the traction mechanism to the arm.

9. The stationary ergometric exercise apparatus according to claim 1, wherein the variables calculated on the basis of signals delivered by the measuring unit are output on the basis of the times of load alternation identified by the measuring device to the right or left limb respectively.

10. The stationary ergometric exercise apparatus according to claim 1, wherein the flywheel includes a braking device that acts by air resistance and is joined to an electro-magnetically-acting brake.

11. The stationary ergometric exercise apparatus according to claim 10, wherein the braking device is located in a housing having means for adjusting the quantity of air being moved as a result of the motion of the flywheel.

12. The stationary ergometric exercise apparatus according to claim 11, wherein the housing has openings, the size and/or air permeability of which is changeable in order to adjust the flow of air passing through the housing.

13. The stationary ergometric exercise apparatus according to claim 10, wherein the braking device is a paddle wheel that is joined in a rotationally locked manner to the flywheel.

14. The stationary ergometric exercise apparatus according to claim 13, wherein the paddle wheel has a plurality of paddle blades aligned parallel to an axis of rotation of the flywheel.

15. The stationary ergometric exercise apparatus according to claim 1, wherein the drive elements are foot-driven pedals.

16. The stationary ergometric exercise apparatus according to claim 1, wherein said pair of sensor devices are the only sensor devices used for apportioning the variables calculated on the basis of the signals delivered by the measuring unit alternately to a right or left limb of a person in training.

17. A stationary ergometric exercise apparatus with a hand- or foot-operable drive with two alternately-operable drive elements wherein the drive is joined to a flywheel by means of a gear mechanism, the apparatus including a measuring unit for measuring at least one of a drive force applied via the drive and a torque related to the drive force and a measuring device for detecting load alternation between the alternately operable drive elements, characterized in that the apparatus includes a wheel joined to the drive so as to be synchronous in motion with the drive and the measuring device includes at least a first sensor, a second sensor, a first sensor piece, and a second sensor piece, the first and second sensor and the first and second sensor pieces being positioned such that at each position in motion of a load alternation, one of the first sensor and second sensor is located exactly opposite one of the first sensor piece and second sensor piece in a direction of the diameter of the wheel and the other of the first sensor and second sensor is aligned with the other of the first sensor piece and second sensor piece in a direction of the diameter of the wheel, the first and second sensors being movable relating to the first and second sensor pieces during operation of the drive, and further characterized by an evaluation device configured to receive signals from the measuring unit concerning the drive force applied and/or torque related to it, and to calculate and continuously output temporal progress of the drive force and/or related torque, as well as variables derivable from the drive force, on the basis of the signals delivered by the measuring unit, and wherein the evaluation device is configured to receive signals from the measuring device identifying times of load alternation between the alternately operable drive elements, and use the times of load alternation identified by the measuring device to apportion the variables calculated on the basis of the signals delivered by the measuring unit alternately to a right or left limb of a person in training.

18. The stationary ergometric exercise apparatus according to claim 17, wherein the first and second sensors and the first and second sensor pieces are the only sensors and sensor pieces used for apportioning the variables calculated on the basis of the signals delivered by the measuring unit alternately to a right or left limb of a person in training.

\* \* \* \* \*

UNITED STATES PATENT AND TRADEMARK OFFICE
CERTIFICATE OF CORRECTION

PATENT NO. : 8,641,581 B2  
APPLICATION NO. : 12/675150  
DATED : February 4, 2014  
INVENTOR(S) : Bacanovic et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this

Twenty-second Day of September, 2015

Michelle K. Lee
*Director of the United States Patent and Trademark Office*